(12) United States Patent
Farrell et al.

(10) Patent No.: US 12,257,369 B2
(45) Date of Patent: Mar. 25, 2025

(54) CATHETER ASSEMBLIES WITH INTERFACIAL pH CONTROLLER

(71) Applicant: Hollister Incorporated, Libertyville, IL (US)

(72) Inventors: David J. Farrell, Ballina (IE); Kevin Murnaghan, Ballina (IE); Carlos Horkan, Westport (IE); Satwinder S. Panesar, Foxford (IE); Paul Healy, Claremorris (IE)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 18/032,292

(22) PCT Filed: Nov. 2, 2021

(86) PCT No.: PCT/US2021/057664
§ 371 (c)(1),
(2) Date: Apr. 17, 2023

(87) PCT Pub. No.: WO2022/103619
PCT Pub. Date: May 19, 2022

(65) Prior Publication Data
US 2023/0390464 A1    Dec. 7, 2023

Related U.S. Application Data

(60) Provisional application No. 63/113,707, filed on Nov. 13, 2020.

(51) Int. Cl.
*A61L 29/02* (2006.01)
*A61L 29/10* (2006.01)
*A61M 25/00* (2006.01)

(52) U.S. Cl.
CPC ............. *A61L 29/02* (2013.01); *A61L 29/106* (2013.01); *A61M 25/002* (2013.01); *A61M 25/0045* (2013.01); *A61L 2400/10* (2013.01)

(58) Field of Classification Search
CPC .... A61L 29/02; A61L 29/106; A61L 2400/10; A61M 25/00; A61M 25/002; A61M 25/0045
USPC .................................................. 206/205, 364
See application file for complete search history.

(56) References Cited

U.S. PATENT DOCUMENTS

| 4,941,308 A * | 7/1990 | Grabenkort ......... A61M 25/002 |
| | | 53/445 |
| 7,066,912 B2 | 6/2006 | Netsenborg et al. |
| 7,476,223 B2 | 1/2009 | McBride |
| 8,177,774 B2 | 5/2012 | House |
| 8,703,048 B2 | 4/2014 | Nielsen et al. |
| | (Continued) | |

FOREIGN PATENT DOCUMENTS

| EP | 1714665 B1 | 8/2011 |
| WO | 2019222644 A1 | 11/2019 |
| WO | 2020106812 A1 | 5/2020 |

OTHER PUBLICATIONS

International Search Report and Written Opinion for International Application No. PCT/US2021/057664 Dated Feb. 23, 2022.

*Primary Examiner* — Bryon P Gehman
(74) *Attorney, Agent, or Firm* — Cook Alex Ltd.

(57) ABSTRACT

Catheter assemblies including an interfacial pH controller for maintaining hydration liquid pH are provided.

21 Claims, 4 Drawing Sheets

(56) References Cited

U.S. PATENT DOCUMENTS

| | | |
|---|---|---|
| 8,747,882 B2 | 6/2014 | Utas et al. |
| 9,192,741 B1 | 11/2015 | Najibi |
| 9,610,384 B2 | 4/2017 | Belt et al. |
| 10,112,031 B2 | 10/2018 | Matthiassen |
| 10,561,817 B2 | 2/2020 | Hannon et al. |
| 2004/0074794 A1 | 4/2004 | Conway et al. |
| 2005/0015076 A1 | 1/2005 | Giebmeyer et al. |
| 2005/0214376 A1 | 9/2005 | Faure et al. |
| 2006/0240069 A1 | 10/2006 | Utas et al. |
| 2007/0244449 A1 | 10/2007 | Najafi et al. |
| 2009/0221989 A1 | 9/2009 | Najafi et al. |
| 2009/0240214 A1 | 9/2009 | Conway et al. |
| 2011/0114520 A1 | 5/2011 | Matthison-Hansen |
| 2012/0289942 A1 | 11/2012 | Becker et al. |
| 2014/0190846 A1 | 7/2014 | Belt |
| 2014/0221522 A1* | 8/2014 | Antoni .................. A61L 29/16 523/105 |
| 2018/0000993 A1 | 1/2018 | Zhang |
| 2019/0001098 A1 | 1/2019 | Utas et al. |
| 2019/0083746 A1 | 3/2019 | Murray et al. |
| 2019/0151610 A1 | 5/2019 | Fletter |
| 2019/0216985 A1 | 7/2019 | McBurney et al. |
| 2020/0038535 A1 | 2/2020 | Montes De Oca et al. |
| 2020/0054795 A1 | 2/2020 | Farrell et al. |
| 2020/0146871 A1 | 5/2020 | Palmer |
| 2020/0230295 A1* | 7/2020 | Mannarino ........... A61L 29/041 |

\* cited by examiner

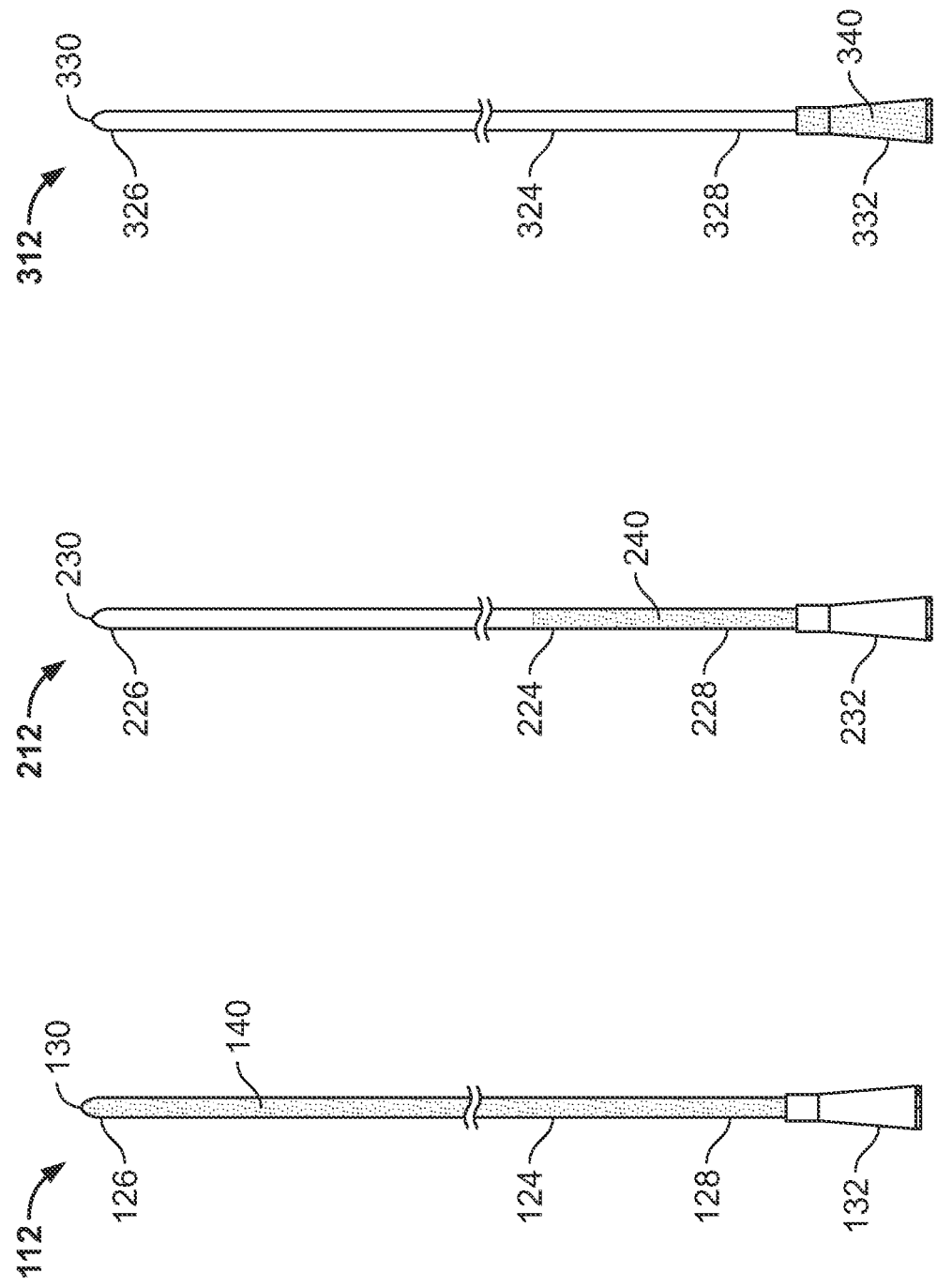

CATHETER ASSEMBLIES WITH INTERFACIAL pH CONTROLLER

CROSS-REFERENCE TO RELATED APPLICATION

The present application is the U.S. National Stage Application of PCT Application No. PCT/US2021/057664, filed Nov. 2, 2021, which claims the benefit of and priority to U.S. Provisional Patent Application Ser. No. 63/113,707, filed Nov. 13, 2020 the content of which is incorporated herein by reference.

DESCRIPTION

Technical Field

The present disclosure generally relates to catheter assemblies for maintaining a desired pH within the package, and more particularly, for catheter assemblies with a pH controller comprising a salt for maintaining a desired pH within the package.

Background

Catheters are used to treat many different types of medical conditions and typically include an elongated catheter shaft that is inserted into and through a passageway or lumen of the body. Catheters, and in particular intermittent catheters, are commonly used by those who suffer from various abnormalities of the urinary system, such as urinary incontinence.

Catheters may have a coating of hydrophilic material applied to the surface of the catheter to provide a lubricious surface. When the hydrophilic material is wetted or hydrated with a hydration medium, the hydrophilic material becomes extremely lubricous. Therefore, it may be particularly advantageous to package a hydrophilically coated urinary catheter with a hydration medium. The hydration medium may be, for example, liquid or vapor water or an aqueous solution. In the field of insertable medical devices, the lubriciousness of the hydrophilic coating can ease introduction of the device into the body and aids in reducing pain and discomfort associated with such introduction.

In catheter packages that are stored in and/or hydrated with a hydration medium, the product may be stored for an extended amount of time in contact with the hydration medium. Additionally, the catheter packages may be sterilized after addition of the hydration medium to the package. The sterilization and/or extended storage time may affect the pH of the hydration medium. It has been found that maintaining the pH range in the package is desirable for a number of reasons and variance in pH may affect the stability of the hydrophilic coating of the catheter, as well as other catheter assembly properties.

In the past, maintaining the pH in a catheter assembly has been accomplished by introducing a buffer system (weak acid and conjugate base or weak base and conjugate acid) to the hydration medium of the catheter assembly. An example of this system is discussed in U.S. Pat. No. 8,703,048 to Coloplast. The system is complicated and requires close attention to buffer levels so as to not cause further irritation in the urethra of the user.

Therefore, there remains a need for improved methods and systems of adjusting/controlling the pH in a catheter assembly.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a catheter assembly includes a package defining a cavity, a catheter with at least a portion of the catheter having a hydrophilic surface contained within the cavity of the package, a hydration liquid within the cavity of the package, and an interfacial pH adjuster or controller comprising a salt at least partially in contact with the hydration liquid of the cavity.

In another aspect, a method of maintaining pH within a catheter package includes placing a catheter with at least a portion including a hydrophilic surface into a catheter package, adding a hydration liquid to the catheter package, and adding an interfacial pH adjuster or controller comprising a salt to the catheter package so it is at least partially in contact with the hydration liquid of the catheter package.

BRIEF DESCRIPTION OF DRAWINGS

FIG. 3 is a side elevational view of a catheter according to one embodiment of the current disclosure.

FIG. 4 is a side elevational view of another catheter according to one embodiment of the current disclosure.

FIG. 5 is a side elevational view of another catheter according to one embodiment of the current disclosure.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
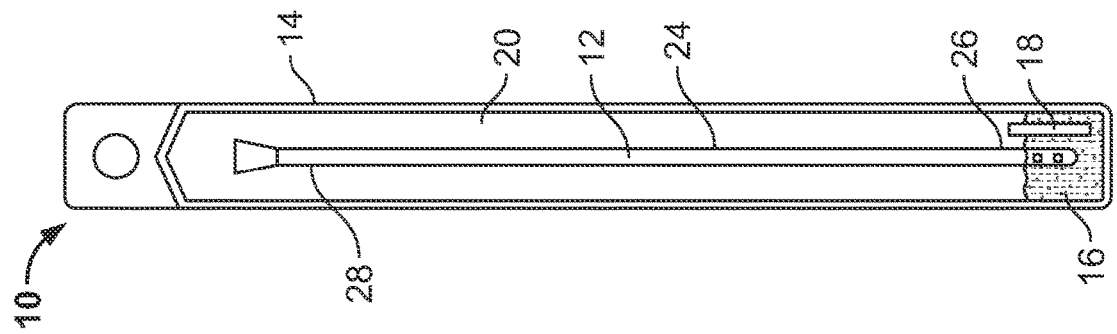
FIG. 1 is a front plan view of a catheter assembly according to one embodiment of the current disclosure.

Referring to FIG. 1, as an example, the present disclosure is directed to catheter assemblies 10 with packages 14 defining a cavity 20 that include a catheter 12 with tubing 24 that may be inserted into and advanced within a lumen of a body, such as a urethra, a hydration liquid 16 within the cavity, and a interfacial pH controller (not shown). The catheter 12 has a proximal insertion end 26 and distal end 28 that can include a drainage member or funnel. Although the fluid is shown in the package near the proximal end, it may be configured alternatively and at varying levels or amounts.

The catheter 12, and specifically the tubing 24, can be made from a polymer material. The polymer material can be any known in the art including, but not limited to, polyolefins and/or thermoplastic elastomers, such as polyvinyl chloride, polyethylene, polyurethane, block copolymers, and polypropylene. The catheter 12 and catheter tubing 24 may have a straight or arcuate configuration, such as a coiled, wound, bent or curved configuration. In the coiled configuration, the catheter may be in a circular, oval or elliptical configuration. The catheter 12 may be any suitable urinary catheter used for bladder drainage. The catheter 12 has a proximal end which can include an introducer tip for insertion and a distal end which can include a drainage member or funnel.

The catheter 12 may be a hydrophilic catheter wherein the catheter tubing 24 may include a hydrophilic coating. When the hydrophilic coating is wetted or hydrated with a hydration medium, such as water, it becomes lubricious which eases introduction of the device into the body and aids in reducing pain and discomfort associated with such introduction. The hydrophilic coating can be a single layer or multilayer hydrophilic coating. Multiple layered coating can include at least a base coat and top layer. The hydrophilic materials of the hydrophilic coating may be materials that become lubricious when hydrated, activated or wetted with a hydration medium. The lubricious hydrophilic material may include any suitable hydrophilic polymer such as, polyvinylpyrrolidone, polyethylene oxide, polyurethanes, homo- and copolymers of acrylic and methacrylic acid, polyvinyl alcohol, etc. The hydrophilic material may be a coating on the surface of the catheter.

The catheter assembly 10 includes a catheter package 14 with a cavity 20. The package 14 is preferably liquid and gas impermeable and may be made from any suitable liquid and gas impermeable materials, such as foils, polymers or multilayer films or laminates containing layers of metallic and/or polymer materials. The package 14 may be sufficiently liquid and gas impermeable so as to provide the catheter assembly 10 with a shelf life of six months to three years.

In one embodiment, the package 14 is made from aluminum foil. In another embodiment, the package 14 is made from a polymer film. In yet another embodiment, the package 14 is made from a multilayered film including a polymer overlaying a foil, such as polypropylene covered aluminum foil. In the embodiments illustrated in the included figures, the package 14 is generally rectangular. The package 14 also may be shapes other than rectangle. For example, the package 14 may be generally round (e.g. circular, oval, ellipse, etc.) or generally square.

The cavity 20 of the catheter package 14 may include a hydration liquid 16. When the catheter 12 is a hydrophilic catheter, the package 14 may include one or more sources for hydrating the hydrophilic surface of the catheter 12 while the catheter 12 is stored within the package 14. An amount of hydration liquid 16, or wetting fluid, for contacting and hydrating the hydrophilic surface of the catheter 12 may be contained (or provided) within the cavity 20 of the package 14. In an alternative embodiment, an amount of vapor donating liquid that provides a hydration vapor for vapor hydrating the hydrophilic surface of the catheter 12 may be disposed within cavity 20 of the package 14. The hydration liquid 16 may be water or an aqueous solution. The hydration liquid 16, or wetting fluid, may include water and a number of additives. Additives can include stability compounds or antioxidants including, but not limited to, glycerol, tocopherols, and ascorbic acid. Hydration liquid 16 can also include hydrophilic polymers. The hydration liquid 16 of the present disclosure may also optionally include one or more of a surface tension reducing agent, mucilage, deep eutectic liquid, oil and osmolality increasing agents. Any of the hydration liquids disclosed herein may be used in a foamed or unfoamed state.

The catheter assembly also may include a thin flexible sleeve 442 (FIG. 6) that covers at least a section of the outer surface of the catheter 412. The sleeve 442 may be formed of any variety of thin flexible polymeric film materials, such as polyethylene, plasticized PVC, polypropylene, polyurethane or elastomeric hydrogels. When the catheter 412 includes a hydrophilic coating thereon, the sleeve 442 may be liquid and/or vapor permeable so as to allow liquid and/or vapor therethrough to hydrate the hydrophilic coating while the catheter is stored within the package. Alternatively, the sleeve 442 may include a hydration liquid or a foamed hydration liquid within the sleeve and in contact with the hydrophilic material.

The catheters and catheter assemblies of the present disclosure may be sterilized prior to use. The catheter assemblies may be sterilized by applying a sufficient amount of radiation, such as gamma or E-Beam radiation. In one embodiment, the packages are electron beam sterilized at 10 MeV with a dose in the range of 25-65 kGy. The catheter assemblies can be sterilized with radiation while the hydrophilic coating is in contact with the wetting fluid.

The catheter assembly may further include an interfacial pH controller, which also may be considered a pH adjuster, that controls and/or adjusts the pH of the hydration liquid contained within the package. The pH controller is not shown in FIG. 1, but may be incorporated into any suitable surface of the catheter assembly. For example, the pH controller may be incorporated into the varying surfaces as shown in the remaining figures. In one embodiment, the interfacial pH controller may be any salt effective for controlling pH. The pH controller controls or adjusts the pH by coming into direct contact with the hydration liquid of the package. When the liquid comes into direct contact with the pH controller, a neutralization reaction occurs at the interface. In particular, when the hydration liquid that contains an acidic solute comes into contact with the surface of the pH controller, it adjusts by the mechanism of neutralization. Acidic solutes, such citric acid or other acids may be purposefully included in the hydration fluid to inhibit bioburden development in the hydration fluid before inclusion of an aliquot of the hydration fluid into the catheter product during manufacturing. Additionally, acidic solutes, such as carbonic acid from air or acidity derived from the hydrophilic coating itself or raw materials used in the hydration fluid, or acidic impurities therein may result in pH drop of the hydration fluid before or after its inclusion in the finished product configuration. Furthermore, low concentrations of acidic solutes, such as hydrogen chloride, may form in the hydration liquid by, for example, a chain scission mechanism when PVC (polyvinyl chloride) is exposed to high-energy radiation.

The neutralization process occurs when acidic solutes, in intimate contact with the pH controller react to form water and salts. For example, if the pH controller contains calcium carbonate, the soluble acid can react with calcium carbonate ($CaCO_3$) to form water, carbon dioxide, and soluble calcium salts. This is shown by the following equation:

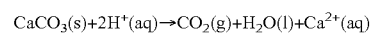

The interfacial pH controller functions to maintain the pH of the hydration fluid of the package in the 4.5 to 8.0 pH range, preferably 6.0 to 7.5 pH range. The range of pH maintained can be tailored by varying the amount of pH controller and/or the total surface area of the pH controller that comes into contact with the liquid. During sterilization of the catheter assembly, the pH of the hydration fluid may adjust upward or downward outside of the desired range. For example, when the catheter assembly is exposed to sterilizing radiation, such radiation may cause the pH to decrease. However, surprisingly, the addition of the interfacial pH controller prevents (or inhibits) the pH from changing during sterilization and storage thereafter.

The interfacial pH controller may be a salt with a low solubility in pure water and adjusts/controls the pH. The pH controller may have a solubility of less than 0.005 wt % at 25° C. or preferably less than 0.003 wt % at 25° C. For example, calcium carbonate has very low solubility in water. Calcium carbonate has a solubility in water at 25° C. of c. 14 mg/l or less than 0.002 wt %. Similarly, Calcium Phosphate, $Ca_3(PO_4)_2$, has a solubility in water at 25° C. of 25 mg/l or less than 0.003 wt % in water. The interfacial pH controller may be an inorganic salt, which includes a cation and an anion. The cation can be an alkaline earth metal such as beryllium, magnesium, calcium, barium. In some alternative examples, the alkaline earth metal is calcium or magnesium. The anion can include chloride, nitrate, sulfates, carbonate, and phosphate. In some alternative examples, the anion is carbonate or phosphate. For example, inorganic salts may include magnesium carbonate and calcium phosphate. A particularly useful salt is calcium carbonate. The salt can be in a film, pill, powder, or any other known form.

The pH is maintained in the catheter assembly by adding an interfacial pH controller comprising a salt to the catheter package so it is at least partially in contact with the hydration liquid of a catheter package.

The interfacial pH controller may be added to the catheter assembly in a number of ways. The interfacial pH controller may be incorporated into or associated with a film. The interfacial pH controller can be embedded in the polymer film, such as before the film is formed by extrusion, lamination or another process. The interfacial pH controller may also be coated on or incorporated into the film after its formation. The film can be a polymer film. The film can be single or multilayer, with the interfacial pH controller in/on one or more layers of the film.

The polymer can be polyethylene, polyurethane, polypropylene, or any combination of these polymers or other suitable polymers. The film can be 10-50 microns, preferably about 25 microns. The interfacial pH controller may also be in pill form. The film or pill may be placed into the cavity of the package. It can be secured to a wall of the package or free floating in the package.

The interfacial pH controller may also be associated with the catheter or part of the catheter package of the catheter assembly. In one embodiment, this association is by embedding the interfacial pH controller into at least one layer of the catheter or catheter packaging. The embedding may be done after the layer is formed or the interfacial pH controller may also be incorporated or embedded with the polymer of the layer before the layer is formed, such as by extrusion, lamination, or some other layer forming process. In another embodiment, this association is by coating the interfacial pH controller onto the surface or a surface layer of the catheter or catheter packaging.

Figure 2:
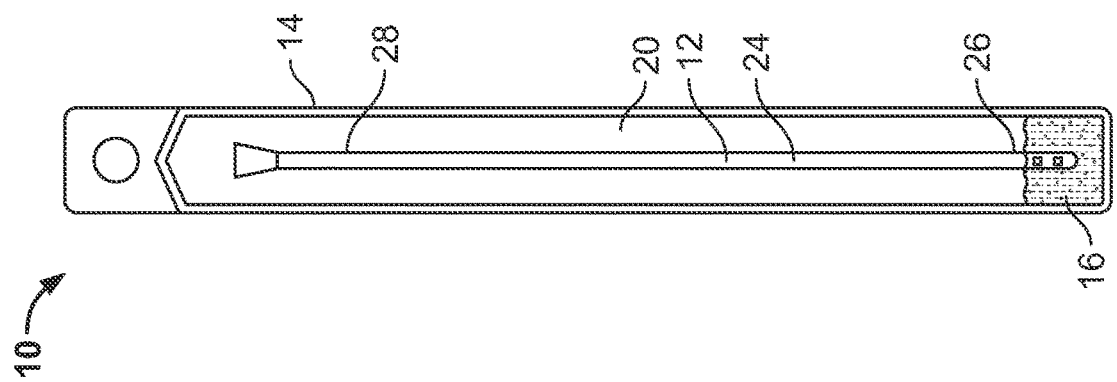
FIG. 2 is a front plan view of a catheter assembly according to one embodiment of the current disclosure.

FIG. 2 illustrates the addition of the interfacial pH controller 18, shown in film or pill form. The interfacial pH controller 18 is in contact with the hydration fluid 16. The interfacial pH controller 18 may be alternately configured depending on the arrangement of the hydration fluid, as long as at least a portion of the interfacial pH controller is in contact with the hydration fluid.

FIGS. 3-5 illustrate several embodiments of associating, by embedding or coating on, the interfacial pH controller with the catheter. Coordinating components are similarly numbered. The catheter 112 of FIG. 3 includes an elongated shaft 124 with a proximal insertion end portion 126 and distal end portion 128. Proximal insertion end portion 126 includes a proximal end insertion tip 130 suitable for insertion into the urethra or other lumen of the body.

The proximal insertion end portion 126 may include draining holes or eyes (not shown). Distal end portion 128 may include a drainage member 132, such as a funnel associated therewith. The drainage member 132 aids with directing urine into a collection receptacle. The interfacial pH controller 140 can be embedded in or coated on the entire shaft 124 of the catheter 112. The interfacial pH controller 140 can be distributed equally or unequally along the shaft, with higher concentration possible at the proximal or distal ends.

The interfacial pH controller can also be associated with only one portion of the catheter shaft. FIG. 4 illustrates an embodiment of a catheter 212 wherein the interfacial pH controller 240 is associated with the distal end portion 228 of the catheter shaft 224. The interfacial pH controller can also be associated with the proximal end portion 226 of the catheter.

The interfacial pH controller can also be associated with the drainage member 332 or funnel of the catheter 312, which is illustrated in the embodiment of FIG. 5.

Figure 6:
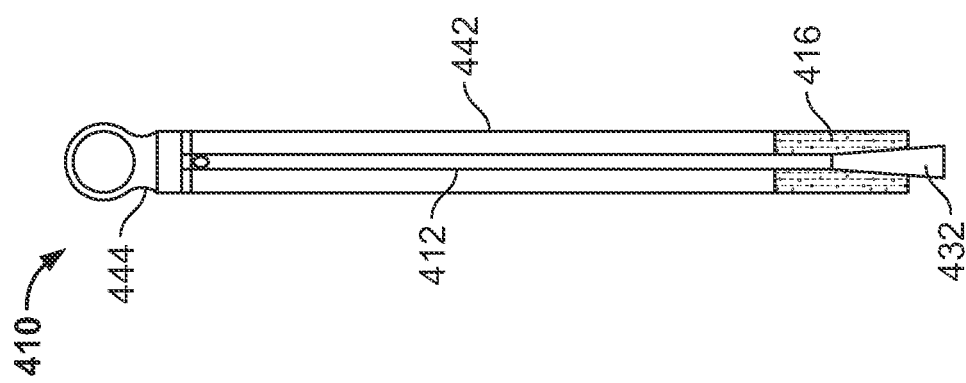
FIG. 6 is a top plan view of another catheter assembly according to one embodiment of the current disclosure.

FIG. 6 illustrates an embodiment of a catheter assembly 410 including a sleeve 442. At least a portion of the catheter 412 is encased with the sleeve 442 that includes a cap 444. An interfacial pH controller, although not visible, can be associated with the sleeve of the catheter assembly. The interfacial pH controller may be embedded within at least one layer of the sleeve or coated onto a surface of the sleeve 442.

Figure 8:
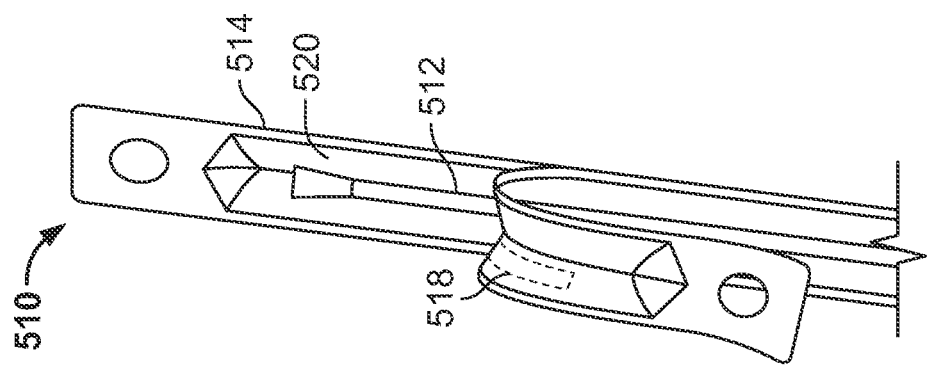
FIG. 8 is a perspective view of the catheter assembly of FIG. 7 in an opened state.
Figure 7:
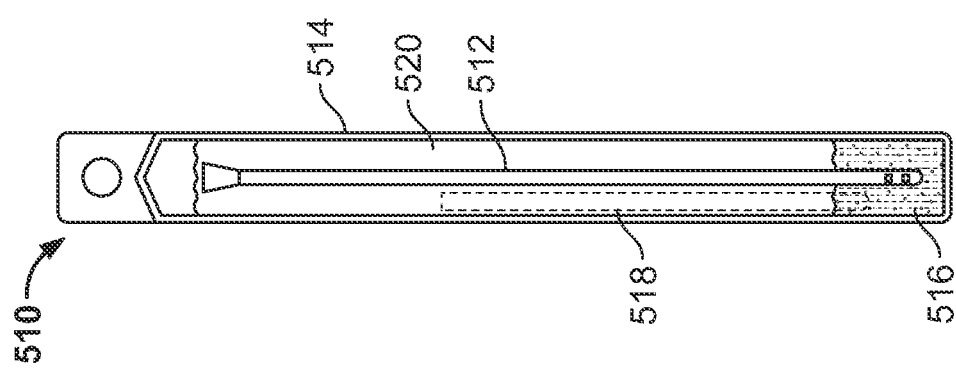
FIG. 7 is a front plan view of another catheter assembly according to one embodiment of the current disclosure.

FIGS. 7-8 illustrate a further embodiment of a catheter assembly, indicated in general at 510. The interfacial pH controller is associated with, embedded in or coated on, a film 518. The film 518 can be attached to the package 514 on an inner surface or layer of the package 514. The cavity 520 includes a catheter and hydration fluid 516.

Figure 9:
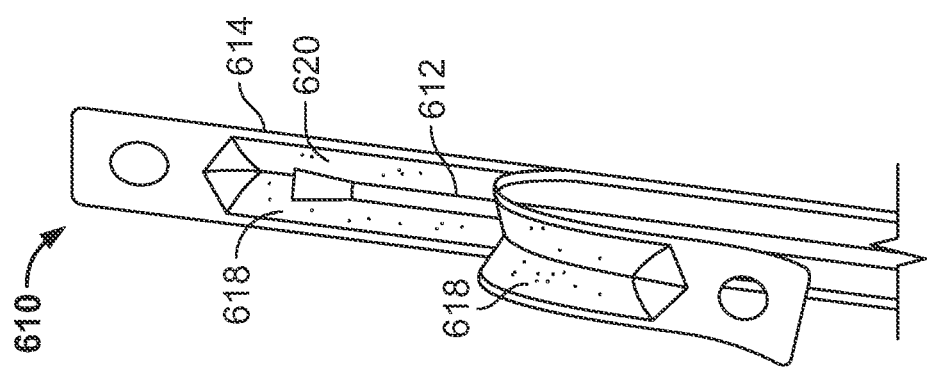
FIG. 9 is a perspective view of another catheter assembly according to one embodiment of the current disclosure.

The film may also be associated with, by embedding in or coating on, the package of the assembly as shown in the catheter assembly 610 of FIG. 9.

Interfacial pH controller 618 is associated with the inner layer or surface of package 614. The interfacial pH controller can be dispersed evenly throughout the package layer or surface within the cavity 620 or can be distributed unevenly and concentrated on either the distal or proximal portion of the package.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A catheter assembly comprising:
   a package defining a cavity;
   a catheter including an insertion portion with at least a portion of the catheter having a hydrophilic surface contained within the cavity of the package;
   a hydration liquid within the cavity of the package; and
   an interfacial pH controller comprising a salt at least partially in contact with the hydration liquid of the cavity, wherein the interfacial pH controller is incorporated into a film that is separate from the insertion portion of the catheter.

2. The catheter assembly of claim 1, wherein the solubility of the salt is less than 0.005 wt % at 25° C. in water.

3. The catheter assembly of claim 1, wherein the salt is comprised of an inorganic salt.

4. The catheter assembly of claim 1, wherein the salt includes an alkaline earth metal.

5. The catheter assembly of claim 4, wherein the alkaline earth metal is calcium or magnesium.

6. The catheter assembly of claim 1, wherein the salt includes an anion.

7. The catheter assembly of claim 6, wherein the anion is carbonate or phosphate.

8. The catheter assembly of claim 1, wherein the salt is at least one of calcium carbonate, magnesium carbonate, and calcium phosphate.

9. The catheter assembly of claim 1 wherein the interfacial pH controller is associated with the catheter.

10. The catheter assembly of claim 1, where the interfacial pH controller is associated with the catheter package.

11. The catheter assembly of claim 1, wherein the film is within the cavity of the package.

12. The catheter assembly of claim 1, wherein the film is attached to the package.

13. The catheter assembly of claim 1, further comprising a sleeve and wherein the film at least partially defines the sleeve.

14. The catheter assembly of claim 1, wherein the film includes a polymer.

15. The catheter assembly of claim 14, wherein the polymer is polyethylene or polyurethane.

16. The catheter assembly of claim 1, wherein the pH of the hydration liquid with the interfacial pH controller is from about 4.5 to 8.0.

17. A catheter assembly comprising:
    a package defining a cavity;
    a catheter with at least a portion of the catheter having a hydrophilic surface contained within the cavity of the package;
    a hydration liquid within the cavity of the package; and
    an interfacial pH controller in pill form comprising a salt at least partially in contact with the hydration liquid of the cavity.

18. The catheter assembly of claim 17, wherein the pill is within the cavity of the package.

19. The catheter assembly of claim 18, wherein the pill is secured to a wall of the package.

20. The catheter assembly of claim 18, wherein the pill is free floating in the package.

21. A method of maintaining pH within a catheter package comprising:
    placing a catheter with an insertion portion with at least a portion including a hydrophilic surface into a catheter package;
    adding a hydration liquid to the catheter package; and
    adding an interfacial pH controller comprising a salt to the catheter package so it is at least partially in contact with the hydration liquid of the catheter package, wherein the interfacial pH controller is incorporated into a film that is separate from the insertion portion of the catheter.

* * * * *